US008906688B2

(12) United States Patent
    Antwiler

(10) Patent No.: US 8,906,688 B2
(45) Date of Patent: Dec. 9, 2014

(54) CELL EXPANSION SYSTEM AND METHODS OF USE

(75) Inventor: Glen Delbert Antwiler, Lakewood, CO (US)

(73) Assignee: Terumo BCT, Inc., Lakewood, CO (US)

(*) Notice: Subject to any disclaimer, the term of this patent is extended or adjusted under 35 U.S.C. 154(b) by 974 days.

(21) Appl. No.: 12/102,413

(22) Filed: Apr. 14, 2008

(65) Prior Publication Data

US 2008/0254533 A1    Oct. 16, 2008

Related U.S. Application Data

(60) Provisional application No. 60/911,601, filed on Apr. 13, 2007.

(51) Int. Cl.
    *C12N 5/02*    (2006.01)
    *C12N 5/00*    (2006.01)
    *C12M 1/34*    (2006.01)
    *C12M 1/12*    (2006.01)
    *C12M 1/00*    (2006.01)

(52) U.S. Cl.
    CPC ............. *C12M 41/00* (2013.01); *C12N 5/0068* (2013.01); *C12M 25/12* (2013.01); *C12M 29/16* (2013.01)
    USPC ..................... 435/401; 435/262.5; 435/286.6; 435/403; 435/295.3; 435/297.1

(58) Field of Classification Search
    CPC ...... C12M 29/10; C12M 29/16; C12M 25/12; C12M 27/02; C12M 23/14; C12M 21/04; C12M 35/04; C12M 41/00

USPC ................. 435/289.1, 297.1, 295.3, 401, 402
    See application file for complete search history.

(56) References Cited

U.S. PATENT DOCUMENTS

| 4,647,539 A | 3/1987 | Bach |
| 4,650,766 A | 3/1987 | Harm et al. |
| 4,722,902 A | 2/1988 | Harm et al. |
| 4,750,918 A * | 6/1988 | Sirkar .............................. 95/44 |
| 4,804,628 A | 2/1989 | Cracauer et al. |
| 4,885,087 A | 12/1989 | Kopf |

(Continued)

FOREIGN PATENT DOCUMENTS

| EP | 0220650 | 5/1987 |
| EP | 1538196 | 6/2005 |

(Continued)

OTHER PUBLICATIONS

International Search Report for PCT/US2008/060209, filed Apr. 14, 2008; Search Report mailed Feb. 17, 2009.

(Continued)

*Primary Examiner* — Michael Hobbs
(74) *Attorney, Agent, or Firm* — Elizabeth J. Reagan; René A. Pereyra; John R. Merkling

(57) ABSTRACT

Cell expansion systems are provided. The cell expansion systems generally include a hollow fiber cell growth chamber, and first and second fluid flow paths associated with the interior of the hollow fibers and exterior of the hollow fibers, respectively. The hollow fibers have a hydrophilic interior surface and a hydrophobic exterior surface. Detachable flow circuits are also provided.

20 Claims, 2 Drawing Sheets

(56) References Cited

U.S. PATENT DOCUMENTS

| | | |
|---|---|---|
| 4,889,812 A | 12/1989 | Guinn et al. |
| 4,894,342 A | 1/1990 | Guinn et al. |
| 4,918,019 A | 4/1990 | Guinn |
| 4,940,541 A * | 7/1990 | Aoyagi .................. 210/321.8 |
| 4,973,558 A | 11/1990 | Wilson et al. |
| 5,079,168 A | 1/1992 | Amiot |
| 5,126,238 A | 6/1992 | Gebhard et al. |
| 5,162,225 A | 11/1992 | Sager et al. |
| 5,202,254 A | 4/1993 | Amiot |
| 5,330,915 A | 7/1994 | Wilson et al. |
| 5,399,493 A | 3/1995 | Emerson et al. |
| 5,416,022 A | 5/1995 | Amiot |
| 5,437,994 A | 8/1995 | Emerson et al. |
| 5,459,069 A | 10/1995 | Palsson et al. |
| 5,510,257 A * | 4/1996 | Sirkar et al. .................. 435/182 |
| 5,541,105 A | 7/1996 | Melink et al. |
| 5,605,822 A | 2/1997 | Emerson et al. |
| 5,622,857 A | 4/1997 | Goffe |
| 5,631,006 A | 5/1997 | Melink et al. |
| 5,635,386 A | 6/1997 | Palsson et al. |
| 5,635,387 A | 6/1997 | Fei et al. |
| 5,643,794 A | 7/1997 | Liu et al. |
| 5,646,043 A | 7/1997 | Emerson et al. |
| 5,656,421 A | 8/1997 | Gebhard et al. |
| 5,670,147 A | 9/1997 | Emerson et al. |
| 5,670,351 A | 9/1997 | Emerson et al. |
| 5,688,687 A | 11/1997 | Palsson et al. |
| 5,763,194 A | 6/1998 | Slowiaczek et al. |
| 5,763,261 A | 6/1998 | Gruenberg |
| 5,763,266 A | 6/1998 | Palsson et al. |
| 5,882,918 A | 3/1999 | Goffe |
| 5,888,807 A | 3/1999 | Palsson et al. |
| 5,981,211 A | 11/1999 | Hu et al. |
| 5,985,653 A | 11/1999 | Armstrong et al. |
| 5,994,129 A | 11/1999 | Armstrong et al. |
| 5,998,184 A | 12/1999 | Shi |
| 6,001,585 A | 12/1999 | Gramer |
| 6,048,721 A | 4/2000 | Armstrong et al. |
| 6,096,523 A | 8/2000 | Parrott et al. |
| 6,096,532 A | 8/2000 | Armstrong et al. |
| 6,197,575 B1 | 3/2001 | Griffith et al. |
| 6,228,635 B1 | 5/2001 | Armstrong et al. |
| 6,238,908 B1 | 5/2001 | Armstrong et al. |
| 6,326,198 B1 | 12/2001 | Emerson et al. |
| 6,372,495 B1 | 4/2002 | Flendrig |
| 6,582,955 B2 | 6/2003 | Martinez et al. |
| 6,616,912 B2 | 9/2003 | Eddleman et al. |
| 6,667,034 B2 | 12/2003 | Palsson et al. |
| 6,680,166 B1 | 1/2004 | Mullon et al. |
| 6,835,566 B2 | 12/2004 | Smith et al. |
| 6,844,187 B1 | 1/2005 | Wechsler et al. |
| 6,943,008 B1 | 9/2005 | Ma |
| 6,969,308 B2 | 11/2005 | Doi et al. |
| 6,979,308 B1 | 12/2005 | McDonald et al. |
| 7,033,823 B2 | 4/2006 | Chang |
| 7,041,493 B2 | 5/2006 | Rao |
| 7,172,696 B1 | 2/2007 | Martinez et al. |
| 7,270,996 B2 | 9/2007 | Cannon et al. |
| 2007/0122904 A1 | 5/2007 | Nordon |
| 2007/0231305 A1 | 10/2007 | Noll et al. |
| 2007/0238169 A1 * | 10/2007 | Abilez et al. .................. 435/325 |

FOREIGN PATENT DOCUMENTS

| | | |
|---|---|---|
| WO | WO86/02379 | 4/1986 |
| WO | WO88/01643 | 3/1988 |
| WO | WO90/02171 | 3/1990 |
| WO | WO91/07485 | 5/1991 |
| WO | WO95/04813 | 2/1995 |
| WO | WO95/21911 | 8/1995 |
| WO | WO00/75275 | 12/2000 |
| WO | WO03/105663 | 12/2003 |
| WO | WO2004/024303 | 3/2004 |
| WO | WO2005/087915 | 9/2005 |

OTHER PUBLICATIONS

Chang et al, "Membrane Bioreactors: Present and Prospects", *Advances in Biochemical Engineering*, 1991, 44:27-64.

Chang, Ho Nam, "Membrane Bioreactors: Engineering Aspects", *Biotech. Adv.*, 1987, vol. 5, pp. 129-145.

Eddington, Stephen M., "New Horizons for Stem-Cell Bioreactors", *Biotechnology*, v. 10, Oct. 1992, pp. 1099-1106.

Gastens et al, "Good Manufacturing Practice-Compliant Expansion of marrow-Derived Stem and Progenitor Cells for Cell Therapy", *Cell Transplantation*, 2007 vol. 16, pp. 685-696.

Gramer et al, "Screening tool for Hollow-Fiber bioreactor Process Development", *Biotechnol. Prog.* 1998, 14, 203-209.

Hirschel et al, "An Automated Hollow Fiber System for the large Scale manufacture of mammalian Cell Secreted Product", in *Large Scale Cell Culture Technology*, ed. Bjorn K. Lydersen, Hanser Publishers, 1987, pp. 113-144.

Nielsen, Lars Keld, "Bioreactors for Hematopoietic Cell Culture", *Annu. Rev. Biomed: Eng.*, 1999,1:129-152.

Pörtner et al, "An Overview on Bioreactor Design, Prototyping and Process Control for Reproducible Three-Dimensional Tissue Culture", in *Drug Testing in Vitro: Breakthroughs and trends in Cell Culture Technology*, ed. Uwe Marx and Volker Sandig, Wiley—VCH, 2007, Chapter 2, pp. 53-78.

Zhao et al, "Perfusion Bioreactor System for Human Mesenchymal Stem Cell Tissue Engineering: Dynamic Cell Seeding and Construct Development", *Biotechnology and Bioengineering*, vol. 91, No. 4, Aug. 20, 2005, pp. 482-493.

* cited by examiner

CELL EXPANSION SYSTEM AND METHODS OF USE

The present application claims benefit under 35 U.S.C. §119(e) to U.S. Provisional Application No. 60/911,601 filed Apr. 13, 2007 which is incorporated herein by reference in its entirety.

FIELD

The present disclosure relates to cell expansion systems (CESs) and associated cell growth chambers.

BACKGROUND

CESs are used to expand, grow, and differentiate cells. The use of stem cells in a variety of potential treatments and therapies have achieved particular attention. Stem cells which are expanded from donor cells can be used to repair or replace damaged or defective tissues and have broad clinical applications for a wide range of diseases. Recent advances in the regenerative medicine field demonstrate that stem cells have unique properties such as high proliferation rates and self-renewal capacity, maintenance of the unspecialized state, and the ability to differentiate into specialized cells under particular conditions.

Cell expansion systems can be used to grow stem cells, as well as other types of cells. There is a need for cell expansion systems that can be used to grow adherent cells, as well as non-adherent cells, and co-cultures of various cell types. The ability to provide sufficient nutrient supply to the cells, remove metabolites, provide sufficient oxygenation to the cells, as well as furnish a physiochemical environment conducive to cell growth in a flexible system is an ongoing challenge.

Many of the cell expansion systems such as the ones discussed above contain both a cell growth module which contains the cells to be expanded, and a separate and distinct oxygenator to supply oxygen to the cells. The cell growth module and the oxygenator are usually separate modules. For ease in manufacturing and use, it would be desirable to have both modules together in one module. The present disclosure addresses these and other needs.

SUMMARY

This invention is directed towards a cell growth module which has a housing with first and second ends which define a longitudinal axis through the housing, and a hollow fiber membrane which has interior and exterior surfaces disposed within the housing. The hollow fiber membrane has a hydrophilic interior surface and a hydrophobic exterior surface. There are at least two ports in the housing which define a first fluid flow path through the interior of the fibers, and at least two ports in the housing defining a second fluid flow path along the exterior of the fibers.

This invention also is directed towards a cell expansion system

DETAILED DESCRIPTION

The present disclosure is generally directed to cell expansion systems and methods of using the same. It should be noted that throughout the description, like elements are depicted by like numerals.

Figure 1:
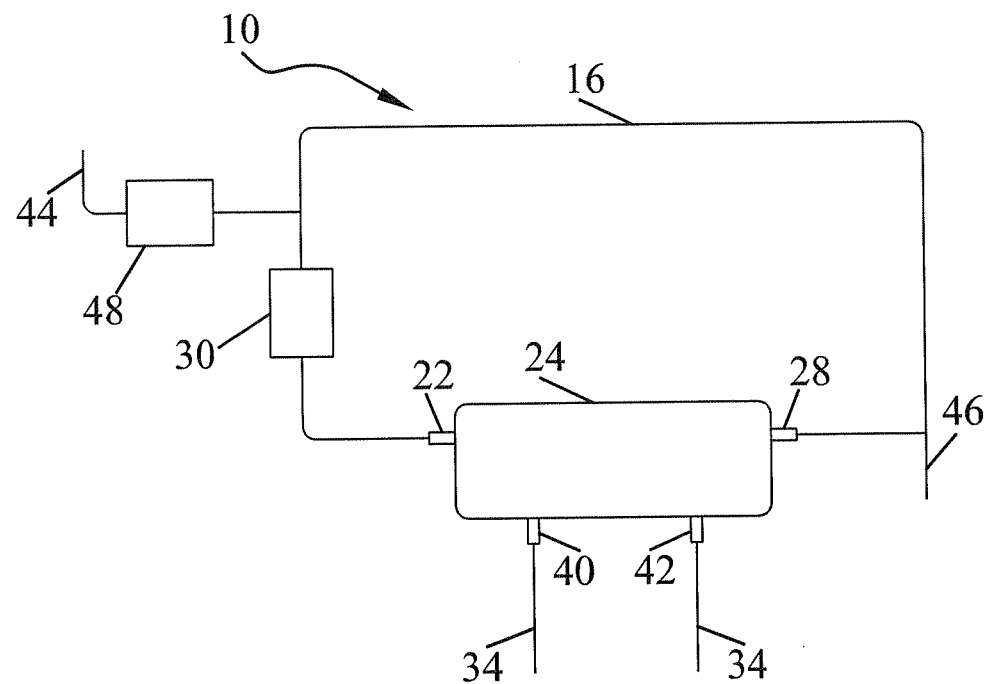
FIG. 1 depicts a flow diagram of one embodiment of a cell expansion system.

An exemplary schematic of a cell expansion system (CES) is depicted in FIG. 1. First fluid flow path 16 is fluidly associated with inlet port 22 of cell growth chamber or module 24 (also referred to herein as a bioreactor) and outlet port 28 of cell growth chamber 24. Fluid flowing through first fluid flow path 16, flows through the interior of hollow fibers or hollow fiber membrane 50 (see FIG. 2) disposed within a housing. The cell growth chamber is described in more detail below. Fluid flow controller 30 is operably connected to first fluid flow path 16, and controls the flow of fluid through the hollow fibers.

A second fluid flow path 34 is fluidly associated with inlet port 42 and outlet port 40 respectively of cell growth chamber 24. Fluid flowing through cell growth chamber 24 in the second fluid flow path 34, flows along the exterior of the hollow fiber membrane 50. A fluid flow controller can optionally be connected to second fluid flow path.

First and second fluid flow paths 16 and 34 are thus separated in cell growth chamber 24 by the hollow fiber membrane 50. Fluid in first fluid flow path 16 flows through the intracapillary ("IC") space of the hollow fibers in the cell growth chamber and is thus referred to as the "IC space." Fluid in second fluid flow path 34 flows through the extracapillary ("EC") space and is thus referred to as the "EC space." Fluid in first fluid flow path 16 can flow in either a co-current or counter-current direction with respect to flow of fluid in second fluid flow path 34.

Fluid inlet path 44 is fluidly associated with first fluid flow path 16. Fluid inlet path 44 allows fluid into first fluid flow path 16, while fluid outlet path 46 allows fluid to leave the cell growth chamber. Fluid flow controller 48 is operably associated with fluid inlet path 44. Alternatively, fluid flow controller 48 can be associated with first outlet path 46.

Fluid flow controllers as used herein can be a pump, valve, clamp, or combination thereof. Multiple pumps, valves, and clamps can be arranged in any combination. In various embodiments, the fluid flow controller is or includes a peristaltic pump.

Various components are referred to herein as "operably associated." As used herein, "operably associated" refers to components that are linked together in operable fashion, and encompasses embodiments in which components are linked directly, as well as embodiments in which additional components are placed between the two linked components. "Operably associated" components can be "fluidly associated." "Fluidly associated" refers to components that are linked together such that fluid can be transported between them. "Fluidly associated" encompasses embodiments in which additional components are disposed between the two fluidly associated components, as well as components that are directly connected. Fluidly associated components can include components that do not contact fluid, but contact other components to manipulate the system (e.g. a peristaltic pump that pumps fluids through flexible tubing by compressing the exterior of the tube).

Cell Growth Chamber

As discussed above, the cell growth chamber of the cell expansion system generally includes a hollow fiber membrane including a plurality of semi-permeable hollow fibers 50 separating first and second fluid flow paths.

Figure 2:
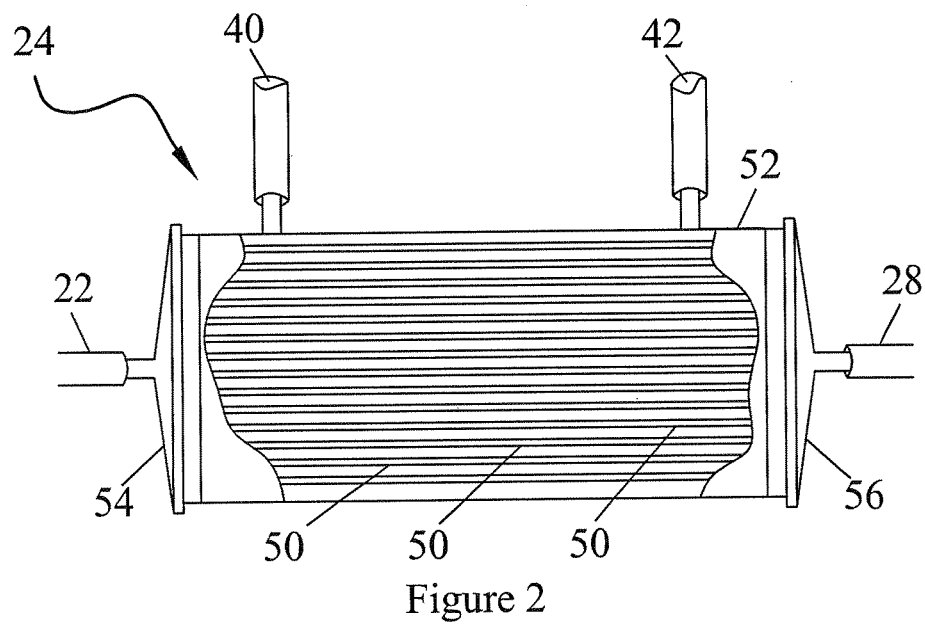
FIG. 2 depicts a side view of a hollow fiber cell growth chamber embodiment of a cell growth chamber.

An exemplary cell growth chamber is depicted in FIG. 2, which depicts a cut-away side view of the hollow fiber cell growth chamber 24. Hollow fibers or membrane 50 are disposed within cell growth chamber housing 52. The housing has first and second ends which define a longitudinal axis through the housing. The housing 52 further includes four openings, or ports: inlet port 22, outlet port 28, inlet port 42, and outlet port 40.

Fluid in the first fluid flow path 16 (see FIG. 1) enters cell growth chamber 24 through inlet port 22, passes into and through the intracapillary space of the hollow fibers and out of cell growth chamber 24 through outlet port 28. The terms "hollow fiber," "hollow fiber capillary," and "capillary" are used interchangeably. A plurality of hollow fibers are collectively referred to as a "membrane." Fluid in the second fluid flow path 34 (FIG. 1) enters the cell growth chamber through inlet port 42, comes in contact with the outside of the hollow fibers, and exits cell growth chamber 24 via outlet port 40.

Cells to be expanded are contained within the first fluid flow path 16 on the IC side of the membrane. The term "fluid" may refer to gases and/or liquids. In an embodiment, a fluid containing liquid such as cell growth media is flown into the first fluid flow path 16, while a fluid containing gas such as at least oxygen is flown into the second fluid flow path 34. The gas diffuses through the membrane from the EC space into the IC space. The liquid however, must remain in the IC space and not leak through the membrane into the EC space.

Although cell growth chamber housing 52 is depicted as cylindrical in shape, it can have any other shape known in the art. Cell growth chamber housing 52 can be made of any type of biocompatible polymeric material.

Those of skill in the art will recognize that the term cell growth chamber does not imply that all cells being grown or expanded in a CES are grown in the cell growth chamber. In many embodiments, adherent cells can adhere to membranes disposed in the growth chamber, or may grow within the associated tubing. Non-adherent cells (also referred to as "suspension cells") can also be grown.

The ends of hollow fibers 50 can be potted to the sides of the cell growth chamber by a connective material (also referred to herein as "potting" or "potting material"). The potting can be any suitable material for binding the hollow fibers 50, provided that the flow of media and cells into the hollow fibers is not obstructed and that liquid flowing into the cell growth chamber through the IC inlet port flows only into the hollow fibers. Exemplary potting materials include, but are not limited to, polyurethane or other suitable binding or adhesive components. In various embodiments, the hollow fibers and potting may be cut through perpendicular to the central axis of the hollow fibers at each end to permit fluid flow into and out of the IC side. End caps 54 and 56 are disposed at the end of the cell growth chamber.

The hollow fibers are configured to allow cells to grow in the IC space of the fibers. The fibers are large enough to allow cell adhesion in the lumen without substantially impeding the flow of media through the hollow fiber lumen.

In various embodiments, cells can be loaded into the hollow fibers by any of a variety of methods, including by syringe. The cells may also be introduced into the cell growth chamber from a fluid container, such as a bag, which may be fluidly associated with the IC side of the cell growth chamber.

Any number of hollow fibers can be used in a cell growth chamber, provided the hollow fibers can be fluidly associated with the inlet and outlet ports of the cell growth chamber.

The hollow fibers may be made of a material which will prevent the liquid contained in the IC space from leaking through the membrane into the EC space, yet must also allow the gasses contained in the EC space to diffuse through the membrane into the IC space. The outside of the fibers therefore may be hydrophobic, while the inside of the fibers may be hydrophilic.

Porous polymeric material which may be used includes polycarbonate, polyethylene sheets containing discrete holes to allow gas through, polypropylene and polytetrafluoroethylene (Teflon). Non-porous material such as silicone may also be used. The material used may be solely of one type, or may be a combination of materials, for example, one type on the inside of the hollow fibers and another type on the outside. The material must be capable of being made into hollow fibers.

In another embodiment, the hollow fibers may be coated with a substance or combinations of substances to make the surfaces hydrophobic and hydrophilic.

The material must also be capable of binding to certain types of cells, such as adherent stem cells (e.g. MSCs). Depending upon the type of cells to be expanded in the oxygenated cell growth chamber, the surface of the fibers in direct contact with the cells to be expanded may be treated with a substance such as fibronectin, platelet lysate or plasma to enhance cell growth and/or adherence of the cells to the membrane.

Cell Expansion Systems

A cell growth chamber such as the one depicted in FIG. 2 is operably associated with other components of a cell expansion system.

Figure 3:
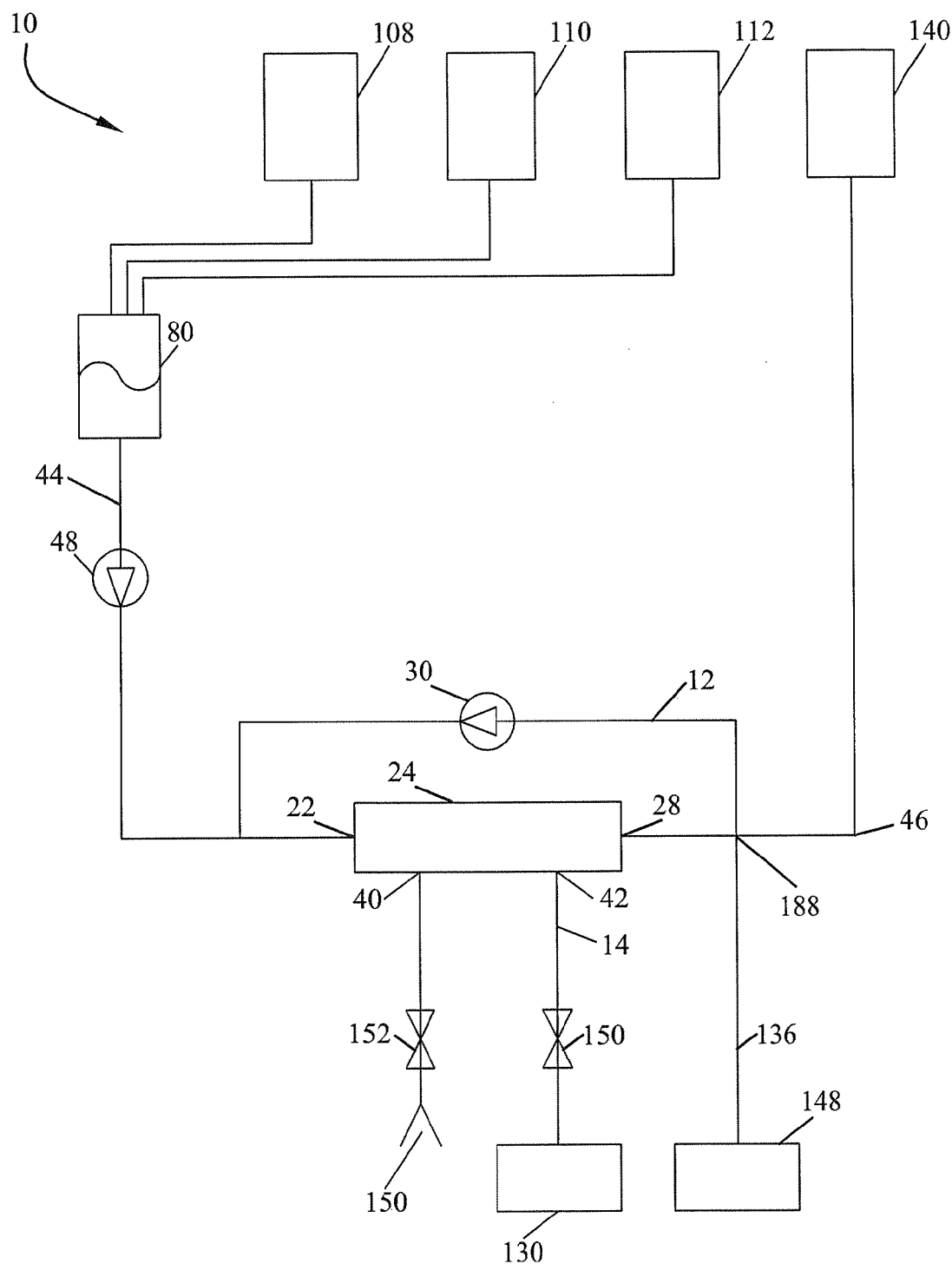
FIG. 3 is a schematic of another embodiment of a cell expansion system.

FIG. 3 depicts a more detailed cell expansion system 10. CES 10 includes first fluid flow path 12 and second fluid flow path 14. Fluid flow paths are constructed of tubing and tubing conduits (Tygothane, St. Globain) and operate in conjunction with valves, pumps and other components (not shown).

Outlet port 28 of cell growth chamber 24 is fluidly associated via tubing with inlet port 22, which together with cell growth chamber 24 form first fluid flow path 12. First fluid flow path 12 is configured to circulate fluid through the IC space of the cell growth chamber 24. First fluid flow path 12 is configured for fluid such as cell growth media to flow through cell growth chamber 24, pump 30, and back through cell growth chamber 24. Cells can be flushed out of cell growth chamber 24 through outlet port 28 to cell harvest bag 140 or can be redistributed back into the IC space via port 22.

CES 10 also includes second fluid flow path 14. Second fluid flow path 14 is configured to flow fluid such as gas through the EC space of the cell growth chamber. The second fluid flow path 14 connects to cell growth chamber 24 by inlet port 42, and departs cell growth chamber 24 via outlet port 40. In the embodiment shown in FIG. 3, gas flows out of gas container or tank 130 into the EC space through port 42, around the hollow fibers of CES 24 and out of the cell growth chamber via port 40. Gas which does not diffuse through the fibers into the IC space, and any carbon dioxide or other gasses which have diffused into the EC space from the IC space flows out of the cell growth chamber through outlet port 40. Gas flows through second fluid flow path at substantially atmospheric pressure. No pump or other means to actively move the gas through the second fluid flow path is needed, as the gas flowing out of tank 130 is under pressure, and once released from the tank, will passively flow at substantially atmospheric pressure. As gas is customarily stored at high pressure, a pressure regulator or orifice or nozzle (not shown) may be placed at the opening of tank 130 to help reduce the initial pressure of the gas flowing out of the tank. The pressure of the gas flowing through the membrane must be at a low enough pressure to avoid formation of gas bubbles within the cell culture chamber 24, but at a high enough pressure to avoid a drop in pressure between inlet port 42 and outlet port 40.

The concentration of gases in the cell growth chamber can be at any concentration desired. Gases diffuse across the fibers in the cell growth chamber. Filters 150 and 152 prevent contamination of the cell growth chamber with airborne contaminants as the gas flows through second fluid flow path 14.

In another embodiment (not shown), a pump could be added to the second fluid flow path 14 to pump the gas containing oxygen through the second fluid flow path. The pump could be located any where on second fluid flow path. Another orifice or pressure regulator could also be placed at the end 150 of second fluid flow path to control any drop in pressure which may occur along the bioreactor and to increase the pressure within the bioreactor.

Liquid media contained in first fluid flow path 12 is in equilibrium with the gases flowing across the membrane from second fluid flow path 14. The amount of gas containing oxygen entering the media can be controlled by controlling the concentration of oxygen. The mole percent (also referred to herein as "Molar concentration") of oxygen in the gas phase before diffusing into the media is typically greater than or equal to 0%, 5%, 10% or 15%. Alternatively, the molar concentration of oxygen in the gas is equal to or less than 20%, 15%, 10% or 5%. In certain embodiments, the molar concentration of oxygen is 5%.

CES 10 includes first fluid inlet path 44. First fluid inlet path 44 includes drip chamber 80 and pump 48. Fluid media and/or cells flow from IC media container 108 and/or cell input bag 112. Each of IC fluid media container 108, vent bag 110, or cell input bag 112 are fluid media containers as discussed herein. IC media refers to media that circulates in first fluid flow path 12.

Drip chamber 80 helps prevent pockets of gas (e.g. air bubbles) from reaching cell growth chamber 24. Ultrasonic sensors (not shown) can be disposed near entrance port and exit port of drip chamber 80. A sensor at entrance port prevents fluids in drip chamber 80 from back-flowing into IC media container 108, vent bag 110, cell input bag 112, or related tubing. A sensor at the exit port stops pump 48 if gas reaches the bottom of the sensor to prevent gas bubbles from reaching the IC side of cell growth chamber 24.

Those of skill in the art will recognize that fluid in first fluid flow path 12 can flow through cell growth chamber 24 in either the same direction as fluid in second fluid flow path 14 (co-current) or in the opposite direction of second fluid flow path 14 (i.e. counter-current).

Cells can be harvested via cell harvest path 46. Cell harvest path 46 is fluidly associated with cell harvest bag 140 and first fluid circulation path 12 at junction 188. Cells from cell growth chamber 24 can be pumped via pump 30 through cell harvest path 46 to cell harvest bag 140.

Various components of the CES can be contained within an incubator (not shown). An incubator would maintain cells and media at a constant temperature.

Fluid outlet path 136 is associated with waste bag 148.

As used herein, the terms "media bag," "vent bag" and "cell input bag" are arbitrary, in that their positions can be switched relative to other bags. For example, vent bag 110 can be exchanged with IC media container 108, or with cell bag 112. The input and output controls and parameters can then be adjusted to accommodate the changes and other media or components can be added to each bag notwithstanding the designation media bag, vent bag, or cell input bag.

Those of skill in the art will further recognize that the pumps and valves in the CES serve as fluid flow controllers. In various embodiments, fluid flow controllers can be pumps, valves, or combinations thereof in any order, provided that the first fluid circulation path and second fluid circulation path are configured to circulate fluid and fluid input path(s) are configured to add fluid.

The CES can include additional components. For example, one or more pump loops (not shown) can be added at the location of peristaltic pumps on the CES. Peristaltic pumps are operably connected to the exterior of tubing, and pumps liquid through the fluid flow path by constricting the exterior of the tubing to push liquid through the tubing. The pump loops may be made of polyurethane (PU) (available as Tygothane C-210A), neoprene based material (e.g. Armapure, St. Gobain), or any other suitable material. Alternatively, a cassette for organizing the tubing lines and which may also contain tubing loops for the peristaltic pumps may also be included as part of the disposable. One or more of the components of the CES can be contained in a cassette to aid in organizing the tubing.

In various embodiments, the CES can include sensors for detecting media properties such as pH, as well as cellular metabolites such as glucose, lactate, and oxygen. The sensors can be operably associated with the CES at any location in the IC loop. Any commercially available pH, glucose, or lactate sensor can be used.

Detachable Flow circuit

A detachable flow circuit is also provided. The detachable flow circuit is a portion of a cell expansion module configured to attach to a more permanent fixed portion of the CES. Generally, the fixed portions of the CES include peristaltic pumps. In various embodiments, the fixed portions of the CES can include valves and/or clamps.

The detachable flow circuit is detachably and disposably mounted to a fluid flow controller. The detachable flow circuit can include detachable fluid conduits (e.g. flexible tubing) that connect portions of the CES. With reference to FIG. 3, the detachable flow circuit includes the tubing for first fluid flow path 12, but without pump 30. In various other permutations, the detachable flow circuit can include tubing that connects the IC media inlet bag 108, vent bag 110, and cell input bag 112 to drip chamber 80. The detachable flow circuit can also include tubing connecting cell harvest bag 140 to first fluid flow path 12. Likewise, the detachable flow circuit can include tubing that makes up second fluid flow path 14. The detachable flow circuit can also include fluid inlet path 44.

The components can be connected together, or separate. Alternatively, detachable flow circuit can include one or more portions configured to attach to fluid flow controllers, such as valves, pumps, and combinations thereof. In variations where peristaltic pumps are used, the detachable circuit module can include a peristaltic loop configured to fit around a peristaltic portion of the tubing. In various embodiments, the peristaltic loop can be configured to be fluidly associated with the circulations paths, inlet paths, and outlet paths.

The detachable flow circuit can be combined in a kit with instructions for its assembly or attachments to fluid flow controllers, such as pumps and valves.

I claim:

1. A cell expansion system comprising:
   a cell growth module comprising:
      a housing having first and second ends defining a longitudinal axis through the housing;

a hollow fiber membrane comprising a plurality of hollow fibers having interior and exterior surfaces, the plurality of hollow fibers being disposed within the housing;
the hollow fiber membrane being held in place within the housing by connective material at the first and second ends of the housing;
each of the plurality of fibers of the hollow fiber membrane further comprising an interior surface comprising a cell adhesion surface on to which cells adhere and an exterior surface, wherein the interior surface is hydrophilic and the exterior surface is hydrophobic;
at least two ports in the housing defining a first fluid flow path through the interior of the fibers;
at least two ports in the housing defining a second fluid flow path along the exterior of the fibers,
wherein the first and second fluid flow paths are separate and distinct from each other;
wherein the first fluid flow path contains cells and at least a liquid and the second fluid flow path contains at least a gas;
wherein the gas contained in the second fluid flow path diffuses through the plurality of hollow fibers into the first fluid path while the liquid contained in the first fluid flow path stays within the first fluid path;
a first container fluidly associated with the first fluid flow path to contain a fluid comprising at least a liquid;
a fluid flow controller operably associated with the first fluid flow path;
a second fluid flow controller operably associated with the first fluid flow path to circulate the at least liquid in the first fluid flow path;
a second container fluidly associated with the first fluid flow path for containing at least liquid removed from the first fluid flow path; and
a third fluid flow controller for flowing a fluid containing at least gas into the second fluid flow path.

2. The cell expansion system of claim 1 further comprising a container fluidly associated with the first fluid flow path containing cells to be expanded in the cell growth module.

3. The cell expansion system of claim 1, wherein the second container comprises expanded cells removed from the cell growth module.

4. The cell expansion system of claim 1 wherein the liquid contained in the first fluid flow path further comprises at least cell growth media.

5. The cell expansion system of claim 1 wherein the gas contained in the second fluid flow path further comprises at least oxygen.

6. The cell expansion system of claim 1 wherein the plurality of fibers in the hollow fiber membrane are each made from a material comprising at least one from the group consisting of polycarbonate, polyethylene, polypropylene, polytetrafluoroethylene, silicone or combinations thereof.

7. The cell expansion system of claim 5 wherein the gas contained in the second fluid flow path comprises less than or equal to 20% molar concentration of oxygen.

8. The cell expansion system of claim 5 wherein the gas contained in the second fluid flow path comprises less than or equal to 15% molar concentration of oxygen.

9. The cell expansion system of claim 5 wherein the gas contained in the second fluid flow path comprises greater than or equal to 5% molar concentration of oxygen.

10. The cell expansion system of claim 1 wherein the plurality of fibers in the hollow fiber membrane are each made from a non-porous material.

11. The cell expansion system of claim 1 wherein the plurality of fibers in the hollow fiber membrane are each made from a porous polymeric material.

12. A method of expanding cells in a cell expansion system, the method comprising:
maintaining within a housing a hollow fiber membrane comprising a plurality of hollow fibers having interior and exterior surfaces, the plurality of fibers being disposed within the housing, wherein the hollow fiber membrane is held in place within the housing by connective material at a first end of the housing and at a second end of the housing, wherein each of the plurality of fibers of the hollow fiber membrane further comprise an interior surface comprising a cell adhesion surface on to which cells adhere and an exterior surface, wherein the interior surface is hydrophilic and the exterior surface is hydrophobic;
defining, by a first plurality of ports in the housing, a first fluid flow path that passes through the interior of the fibers;
defining, by a second plurality of ports in the housing, a second fluid flow path that passes along the exterior of the fibers, wherein the first fluid flow path and the second fluid flow path are separate and distinct from each other;
introducing a liquid and cells into the first fluid flow path, wherein at least a portion of the cells adhere to the cell adhesion surface;
introducing a gas into the second fluid flow path, wherein the gas contained in the second fluid flow path diffuses through the hollow fiber membrane into the first fluid path while the liquid contained in the first fluid flow path stays within the first fluid path;
controlling flow of the liquid within the first fluid flow path with a first fluid flow controller operably associated with the first fluid flow path;
removing at least a liquid from the first fluid flow path; and
controlling flow of at least one gas into the second fluid flow path with a second fluid flow controller.

13. The method of claim 12, wherein the introducing a liquid and cells into the first fluid flow path comprises removing the cells and liquid from a first container associated with the first fluid flow path.

14. The method of claim 12, wherein the removing at least liquid from the first fluid flow path comprises removing expanded cells from the first fluid flow path.

15. The method of claim 12, wherein the liquid in the first fluid flow path further comprises at least cell growth media.

16. The method of claim 10, wherein the gas contained in the second fluid flow path further comprises at least oxygen.

17. The method of claim 16, wherein the gas contained in the second fluid flow path comprises less than or equal to 20% molar concentration of oxygen.

18. The method of claim 16, wherein the gas contained in the second fluid flow path comprises less than or equal to 15% molar concentration of oxygen.

19. The method of claim 16, wherein the gas contained in the second fluid flow path comprises greater than or equal to 5% molar concentration of oxygen.

20. The method of claim 16, wherein the plurality of fibers in the hollow fiber membrane are each made from a material comprising at least one from the group consisting of polycarbonate, polyethylene, polypropylene, polytetrafluoroethylene, silicone or combinations thereof.

* * * * *